United States Patent [19]

Slattery

[11] 4,097,520
[45] Jun. 27, 1978

[54] PREPARATION OF PERACETIC ACID BY OXIDATION OF ACETALDEHYDE

[75] Inventor: Gerald Holmes Slattery, Pasadena, Md.

[73] Assignee: FMC Corporation, Philadelphia, Pa.

[21] Appl. No.: 438,949

[22] Filed: Feb. 1, 1974

Related U.S. Application Data

[63] Continuation of Ser. No. 105,527, Jan. 11, 1971.

[51] Int. Cl.² ........................................ C07C 179/12
[52] U.S. Cl. ............................................. 260/502 A
[58] Field of Search .............. 260/502 A, 700, 610 B; 252/373; 261/133

[56] References Cited

U.S. PATENT DOCUMENTS 2,314,385  3/1943  Bludworth ...................... 260/502 A

FOREIGN PATENT DOCUMENTS 633,033  12/1961  Canada ........................... 260/502 A
678,327  1/1964  Canada ........................... 260/502 A Primary Examiner—Bernard Helfin
Assistant Examiner—Werren B. Lone
Attorney, Agent, or Firm—Charles C. Fellows; Frank Ianno; Pauline Newman

[57] ABSTRACT

This specification discloses a vapor phase process for oxidizing acetaldehyde to peracetic acid, acetic acid being formed as an additional product. Oxygen is used as the oxidizer at concentrations of less than 10% by using excess acetaldehyde and diluting the reaction with recycle gas. Initial mixing of the oxygen with acetaldehyde is done in an explosion-suppression chamber prior to introducing the reaction mixture into a reactor.

3 Claims, 1 Drawing Figure

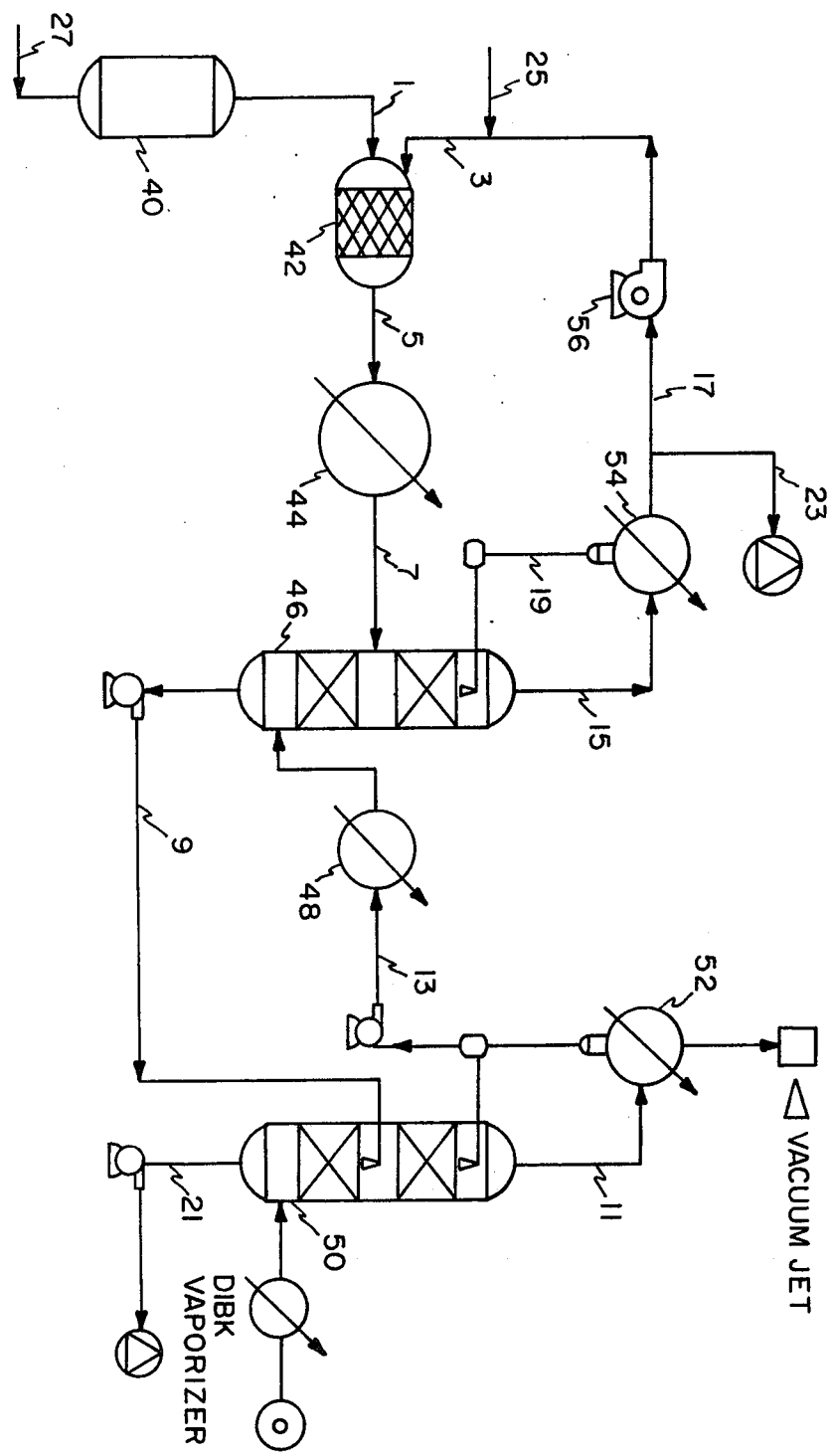

PREPARATION OF PERACETIC ACID BY OXIDATION OF ACETALDEHYDE

This is a continuation of application Serial No. 105,527, filed Jan. 11, 1971.

BACKGROUND OF THE INVENTION

A. Field of the Invention

This invention relates to the vapor phase oxidation of acetaldehyde to peracetic acid.

B. Description of the Prior Art

A vapor phase process for producing peracetic acid by reacting acetaldehyde with oxygen at a temperature of up to 232° C and a pressure of up to 50 lbs. per square inch is disclosed by Bludworth in U.S. Pat. No. 2,314,383, issued Mar. 23, 1943. More recently it has been suggested to feed acetaldehyde and oxygen to a heated aluminum reactor and pass the gaseous reaction product through a fractionating column to rapidly separate peracetic acid product from unreacted acetaldehyde and acetic acid.

The known vapor phase processes are conducted in particular reactor designs. The reactor used by Bludworth and others is a steady-state back-mix flow reactor which contains, as an essential element, a fan, blower or other stirrer capable of creating vigorous mixing throughout the entire reactor volume.

Bludworth disclosed producing about 100 parts by weight per hour of peracetic acid while recycling through the back-mix blower, in a reactor loop, 170 parts per minute (10,000 parts per hour) of hot reaction gases. To produce 400 lbs. of product peracetic acid per hour Bludworth would recycle over 5 tons of hot recycled gas per hour against pressure and within the confines of the reactor loop. The blower in such a process obviously would need to be large and efficient. Blower failure in fan-type, back-mix reactors results in an explosion; this inherent possibility of explosion is one reason why this vapor phase process has not been used extensively. A successful process would require a blower that was large and capable of withstanding an explosion, thus making the blower economically undesirable in terms of high initial cost and expense of operation.

An improved process for the oxidation of acetaldehyde (U.S. patent application Ser. No. 764,079, filed Oct. 1, 1968) discloses a vapor phase process for oxidizing acetaldehyde to peracetic acid, in an elongated reactor into which oxygen is fed through a plurality of oxygen injection sites spaced along the length of the reaction zone. The velocity of passage of the reaction gases through the reaction zone in the areas of the oxygen injection sites is maintained in excess of the flame velocity of the reaction gas mixture and the reaction zone temperature is maintained between about 104° and about 180° C.

It is the principal object of this invention to provide a vapor phase process for oxidizing acetaldehyde to peracetic acid that can be operated safely using almost any reactor configuration such as a back-mix reactor, plug flow reactor with single feed points, or plug flow reactor with multiple point injections and the like.

SUMMARY OF THE INVENTION

I have now discovered that a safe vapor phase process for oxidizing acetaldehyde to peracetic acid is achieved by maintaining the oxygen concentration in the reaction mixture at less than 10 mol%, i.e. 10% by volume, by using excess reactant acetaldehyde and by dilution with recycle gas (acetaldehyde, carbon dioxide, carbon monoxide and oxygen). In my process the oxygen and acetaldehyde reactants are initially mixed externally in a mixer-explosion-suppression chamber constructed like a flame arrestor so that the passage diameter is less than the critical diameter (explosion) for the reaction mixture containing acetaldehyde and oxygen. A further safety factor is achieved by keeping the gas velocity in the explosion-suppression chamber higher than the maximum flame velocity of the reaction mixture. After mixing the reactants, the reaction is conducted in a conventional reaction zone at a temperature of up to 230° C and a pressure of up to 50 pounds per square inch above atmospheric.

DESCRIPTION OF THE INVENTION AND THE PREFERRED EMBODIMENTS

The overall invention encompasses a process in which acetaldehyde is mixed with oxygen, which preferably is ozonated, in an explosion-suppression unit and the reaction mixture is then reacted in a suitable reactor. The product from the oxidation reactor is passed into a peracetic acid absorber column in which acetaldehyde is recovered overhead and peracetic acid is absorbed in a suitable solvent such as acetone. The peracetic acid solution (here discussed as an acetone solution) is introduced into a solvent-switch unit in which the acetone is taken off overhead and the peracetic acid is switched to another material such as a higher boiling solvent, for example disobutylketone, water, xylene or a material to be epoxidized such as allyl alcohol, soybean oil, or any of a number of unsaturated liquids which can be oxidized by an oxygen-addition reaction. The process may also be used for bleaching by switching the peracetic acid into a liquid to be bleached or which serves as a carrier for the peracetic acid which is to be used to bleach other materials or used for other purposes. The acetone from the top of the solvent switch unit is condensed, some of the acetone being refluxed to the solvent switch tower and part of the acetone being vaporized and fed to the peracetic acid absorber where the vaporized acetone functions as a strip gas to effect or assist in the rapid separation of acetaldehyde from the peracetic acid-acetic acid-acetone mixture in the peracetic acid absorber.

The reactants are mixed in the explosion-suppression chamber at below about 100° and preferably below 50° C. The mixed reactants are reacted under conditions that are typical and well known in the art for the vapor phase oxidation of acetaldehyde, i.e. (the reaction is conducted) at a temperature of up to 230° C and a pressure up to 50 pounds per square inch gauge pressure i.e. above atmospheric pressure. Higher temperatures can be used when low conversions can be tolerated by drastically reducing the available oxygen to control excessive oxidation to undesired combustion products. The preferred temperature range is 140° to 180° C and although the reaction can be conducted under pressures up to 50 psi gauge, generally the reaction is conducted only at the pressure necessary to push the reactants through the processing unit, which is generally about 2–14 psi gauge.

Safe operation of the oxidizer-reactor is achieved by maintaining the oxygen concentration in the reaction mixture, immediately after mixing the reactants at less than 10 mol%, i.e. 10% by volume, using excess acetaldehyde and by dilution with recycle gas containing unreacted acetaldehyde, carbon dioxide, carbon monoxide and unreacted oxygen. This can be accomplished in a reactor of any configuration such as a back-mix reactor, a plug flow reactor with a single feed point or a plug flow reactor with multiple feed point oxygen injection. A single point feed oxygen injection plug flow reactor is preferred because the explosive hazard of a mole of oxygen is about as bad as that of the mole of peracetic acid formed so both the oxygen and the peracetic acid concentration should be kept below 10%. Mixing pure and ozonated oxygen with acetaldehyde can create an explosive composition which can easily ignite. This explosion can be prevented (or tolerated and suppressed) by mixing the reactants in an explosion-suppression chamber constructed like a flame arrestor so that the passage diameter is less than the critical diameter (explosion) for the system and material. Columns of aluminum beads, ⅛ inch in diameter, and aluminum or stainless steel packing such as "Goodloe" wire mesh works very well as an effective suppression chamber. A 1 inch diameter tube 5 feet long packed with "Goodloe" aluminum packing is an effective suppression chamber in which acetaldehyde and oxygen can safely be mixed when the oxygen level is kept at 10% or less. Proper control of the oxygen flow in which the oxygen is maintained below 10% and preferably at 5%, makes subsequent explosions impossible in the mixed gas while in the packed mixing device. A further safety factor is achieved by keeping the gas velocity in the explosion suppression chamber higher than the maximum flame velocity of the reaction gas mixture. The reaction gas mixture, after being mixed in the explosion-suppression chamber, is introduced into a reactor. The heat of reaction in the reactor and the required residence time are handled by a simple heat exchanger. Control of the carbon dioxide concentration in the reactor is effected by controlling the recycle gas ratio. This permits higher than nominal oxygen concentration levels because carbon dioxide is an unusally good explosion suppressor.

The gas mixture leaves the reactor and is passed to a peracetic acid absorber which operates safely at all points because the oxygen concentration in the incoming feed gas is already at a safe level. Concentration of peracetic acid at unsafe levels is prevented by avoiding a reboil of the bottoms in the absorber by feeding only acetone gas to the bottom of the absorber. The acetone gas acts as a strip gas which assists in the removal of acetaldehyde from the absorbing liquid and rapidly separates peracetic acid from the acetaldehyde, thereby minimizing reaction of dissolved acetaldehyde and peracetic acid in the absorbing solvent.

Acetone and ethyl acetate are preferred as absorbing liquids because the solvents being un-reactive solvents prevent excessive formation of acetaldehyde monoperacetate. These solvents make possible the production of high concentrations of peracetic acid at good peracetic acid to acetic acid ratios. Moreover, peracetic acid in acetone or ethyl acetate has good stability. Peracetic-acetic acid solution coming from the absorber may be used directly for epoxidation of soybean oil, linseed oil, and other oxidizable liquids that are susceptible to oxidation or epoxidation by peracetic acid in inert solvent solutions.

The solvent-peracetic acid solution from the absorber may pass to a switch tower to remove acetone from the peracetic acid and replace acetone or ethyl acetate solvent with a solvent more suitable for liquid processing steps. Solvents which can be used in a solvent switch tower are diisobutylketone, cumene, water, such as soybean oil, linseed oil, allyl alcohol and organic materials that can be oxidized in oxygen addition reactions as well as liquids that are to be bleached. Operation of the solvent switch tower is conducted safely by eliminating a reboiler (particularly for solvents that boil below peracetic acid) and by utilizing gas feed only of the second solvent. Reduced pressure may be required to reduce peracetic acid thermal degradation to a tolerable level. Little reflux is required in the solvent switch tower as the acetone or ethyl acetate which is removed overhead recycles to the peracetic acid absorber. If the solvent switch column is operated under vacuum and acetone is used as the solvent in the peracetic acid absorber, a compressor can be used to "lift" the acetone back to the peracetic acid absorber. It may be desirable to condense the acetone in vacuum and re-evaporate the acetone for the absorber at the proper pressure should it be desirable to avoid compressors.

The overall process will now be described with reference to FIG. 1 using acetone as a peracetic acid absorbing solvent. Oxygen is fed through line 27 to ozonator 40. Ozonated oxygen from ozonator 40 fed through line 1 to the explosion suppression chamber 42 while acetaldehyde from line 26 is fed through a mixing tee to line 3 and the mixture of acetaldehyde and recycle gas is fed to unit 42 in which the acetaldehyde and ozonated oxygen are mixed. The mixture of reactants and recycle gas leaves unit 42 through line 5 and is fed to reactor 44. The reaction mixture leaves reactor 44 through line 7 and is fed to about the mid-point of the peracetic acid absorber 46. The peracetic acid absorber is also fed with vaporized acetone, from the acetone vaporizer 48, near the bottom of the absorber so that the vaporous acetone acts as a strip gas to facilitate rapid removal of the acetaldehyde from the absorbing solvent. The vaporous acetone leaving the top of the peracetic acid absorber 46 through line 15 is condensed and returned to the peracetic acid absorbers through line 19. The acetaldehyde leaving the top of the peracetic acid absorber 46 does not condense in reflux condenser 54 and is passed on through line 17 to the recycle blower 56 which pumps this recycle gas to a mixing tee where makeup virgin acetaldehyde is added, and all of this gas is recycled through line 3 to the explosion suppression mixing chamber 42. Peracetic acid leaves the bottom of the peracetic acid absorber 46 through line 9 and is fed to the solvent switch tower 50. Vaporous diisobutylketone is fed to the bottom of the solvent switch tower. Acetone leaves the top of the solvent switch tower through line 11 and is condensed in the acetone condenser 52 and returned to the acetone vaporizer through line 13. Peracetic acid and diisobutylketone leave the bott m of the solvent switch tower 50 through line 21. Noncondensed gas and by-product gas passing through reflux condenser 54 are purged from the system through line 23 and sent to the gas recovery unit where the entrained acetaldehyde and oxygen can be recovered.

The invention has numerous advantages. Use of oxygen results in low inert gas and low non-condensible gas loss and simplifies recovery of acetaldehyde from the vent gas, also a smaller acetaldehyde absorber is required; a reactor that cannot explode is utilized, safe oxygen fuel mixing occurs under conditions where the oxygen and acetaldehyde cannot explode; the peracetic acid absorber is operated below the oxygen-acetone explosive limit; safe peracetic acid absorption is effected because there is little or no acetaldehyde monoperacetate produced. The process operates without a reboiler so that it is not possible to concentrate peracetic acid in the reboiler and no air or strip gas compressors or air drying is required.

The following examples illustrating the novel process disclosed herein are given without any intention that the invention be limited thereto. All parts and percentages are by weight unless otherwise specified.

EXAMPLE 1

An explosion suppression device, "Suprex Unit", was constructed of 1 inch 316 stainless steel, schedule 40 pipe packed with a 12 inch long cyliner of aluminum Goodloe wire mesh packing, which resembles steel wool. About 54 pounds of gaseous acetaldehyde and 100 standard cubic feet of oxygen, containing 2.2 miligrams per liter ozone, per hour at 25° C were introduced through a tee leg to the Suprex unit. These gases mixed intimately with an immediate temperature rise to 70° C with no explosion or back fires. These catalyzed reaction gaseous were passed to an aluminum reactor consisting of ten 20-foot sections of jacketed 1-½ inch Sched. 40 aluminum pipe, alloy 6061, T-6 (ASTM B241-67) connected in series. The reactor pressure was maintained at two pounds per square inch gauge (PSIG) and the reactor temperature maintained at 146° to 170° C. No fires or explosions occured and operating conditions were maintained although the mixture was of explosive composition. About 99% of the oxygen was consumed and about 18% of the acetaldehyde was consumed of which 92.5% was converted to peracetic acid and acetic acid at the rate of 16.6 pounds per hour peracetic acid.

Hot effluent gas from the peracetic acid generator at 120°–125° C was passed as the rate of 1.3 pound-mols per hour into the middle of a packed aluminum column (aluminum Goodloe packing) where substantially all of the peracetic acid and acetic acid were absorbed in boiling acetone while the noncondensible gases ($O_2$, $CO_2$, CO) and unreacted acetaldehyde passed out from the top of this column to a refrigerated partial condenser which supplied the required reflux to the absorption cocolumn. The acetone solution of peractic acid and acetic acid passed down through the stripping portion of the column where it was contacted by the incoming acetone which was fed as vapor to the column bottom, thus eliminating the need for a column reboiler with its subsequent hazard of over-concentrating the peracetic acid to a detonable level (above 60% PAA). An acetone solution drawn from the column bottom contained 14.1 pounds per hour peracetic acid, 3.6 pounds per hour acetic acid, about 82 parts acetone, per hour at about 60° C. (column pressure near atmospheric pressure). This hot acetone-peracetic acid solution was then fed to the middle of a solvent-switch column to which a higher boiling (than acetone) alternate solvent (water) was introduced as vapor at the column bottom at the rate of 90 pounds per hour. This hot alternative solvent vapor (water) condensed in the column absorbing the peracetic acid and acetic acid and simultaneously driving off the more volatile acetone to the top of the column where it was condensed and used as reflux with the net make being recycled to the peracetic acid absorption column.

The alternative solvent-solution containing 14 pounds per hour of peracetic acid, 3.7 pounds per hour acetic acid, 90 pounds per hour water were then passed to an epoxidizer for utilization of the peracetic acid. Losses of peracetic acid incurred in the solvent switch column where about 1%

EXAMPLE 2

About 54 pounds per hour of acetaldehyde vapor (virgin acetaldehyde and recycle gas) at 30° C was passed to the entry end of the "Suprex Unit" of Example 1 with 100 SCFH oxygen (30° C) containing 2.2mg/liter ozone also introduced in through a teeleg in the Suprex Unit. These gases mixed intimately with an immediate temperature rise to 70° C with no explosions or backfires and the catalyzed reaction gases then passed to a conventional peracetic acid reactor of the Bludworth type (fan loop unit) operating at 140° to 170° C at 2 PSIG where 99% of the oxygen was consumed and 19% of the acetldehyde was consumed, producing 16.6 pounds per hour peracetic acid.

Hot effluent gas from the peracetic acid generator at 120°–125° C was passed as the rate of 1.3 pound-mols per hour into the middle of a packed aluminum column (aluminum Goodloe packing) where substantially all of the peracetic acid and acetic acid were absorbed in boiling acetone while the noncondensible gases ($O_2$, $CO_2$, CO) and unreacted acetaldehyde passed out from the top of this column to a refrigerated partial condenser which supplied the required reflux to the absorption cocolumn. The acetone solution of peracetic acid and acetic acid passed down through the stripping portion of the column where it was contacted by the incoming acetone which was fed as vapor to the column bottom, thus eliminating the need for a column reboiler with its subsequent hazard of over-concentrating the peracetic acid to a detonable level (about 60% PAA). An acetone solution drawn from the column bottom contained 14.1 pounds per hour peracetic acid, 3.6 pounds per hour acetic acid, about 82 parts acetone, per hour at about 60° C (column pressure near atmospheric pressure). This hot acetone-peracetic acid solution was then fed to the middle of a solvent-switch column to which a higher boiling (than acetone) alternate solvent (water) was introduced as vapor at the column botton at the rate of 90 pounds per hour. This hot alternative solvent vapor (water) condensed in the column absorbing the peracetic acid and acetic acid and simultaneously driving off the more volatile acetone to the top of the column where it was condensed and used as reflux with the net make being recycled to the peracetic acid absorption column.

The alternative solvent-solution containing 14 pounds per hour of peracetic acid, 3.7 pounds per hour acetic acid, 90 pounds per hour water were then passed to an epoxidizer for utilization of the peracetic acid. Losses of peracetic acid incurred in the solvent switch column were about 1%.

This invention has been explained and exemplified in a manner so that it can be readily practiced by those skilled in the art. The best mode contemplated by the inventor has been set forth. Clearly, within the scope of the appended claims, the invention can be practiced by those skilled in the art having the benefit of the disclosure, otherwise than as specifically described and exemplified herein.

What is claimed is:

1. In the process of producing peracetic acid by the vapor-phase oxidation of acetaldehyde in a reaction zone, in which the reactants, acetaldehyde and oxygen, are mixed before introducing the reaction gas mixture into the reaction zone, which is maintained at a temperature of 100° to 230° C at a pressure of up to 50 pounds per square inch, and recovering the product peracetic acid by absorption in a liquid selected from the group consisting of acetone and ethyl acetate, the improvement which comprises: (a) mixing the reactants in a cylindrical mixer-explosion-suppression chamber containing aluminum or stainless steel packing whose passage diameter is less than the critical diameter of the reaction gas mixture, while maintaining the oxygen concentration at less than 10% by volume in said chamber and maintaining the reaction gas velocity in the explosion suppression chamber in excess of the flame velocity of the reaction gas mixture, and (b) introducing the mixed reaction gas mixture into the reaction zone, in which the oxygen concentration in the reaction zone is maintained at less than 10% by volume of the reaction gas mixture.

2. The process of claim 1 in which the reactants are mixed at below 50° C and the reaction temperature is 140° to 180° C.

3. The process of claim 1 in which the absorbing liquid for the peracetic acid is first vaporized and then fed to the bottom of the absorber.

* * * * *

UNITED STATES PATENT AND TRADEMARK OFFICE
CERTIFICATE OF CORRECTION

PATENT NO. : 4,097,520
DATED : June 27, 1978
INVENTOR(S) : Gerald Holmes Slattery It is certified that error appears in the above-identified patent and that said Letters Patent are hereby corrected as shown below:

Column 2, line 30, "disobutylketone" should read --diisobutylketone--; line 62, "2-14" should read --2-15--. Column 4, line 25, "26 is fed through" should read --25 is fed through--. Column 6, line 2, "where" should read --were--; line 16, "acetldehyde" should read --acetaldehyde--.

Signed and Sealed this

Eighth Day of May 1979

[SEAL]

Attest:

RUTH C. MASON
Attesting Officer

DONALD W. BANNER
Commissioner of Patents and Trademarks